(12) United States Patent
Amplatz et al.

(10) Patent No.: US 9,980,709 B2
(45) Date of Patent: *May 29, 2018

(54) PERCUTANEOUS CATHETER DIRECTED INTRAVASCULAR OCCLUSION DEVICE

(71) Applicant: St. Jude Medical, Cardiology Division, Inc., St. Paul, MN (US)

(72) Inventors: Kurt Amplatz, St. Paul, MN (US); Xiaoping Gu, Plymouth, MN (US); John C. Oslund, Blaine, MN (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 330 days.

This patent is subject to a terminal disclaimer.

(21) Appl. No.: 14/157,692

(22) Filed: Jan. 17, 2014

(65) Prior Publication Data

US 2014/0135828 A1 May 15, 2014

Related U.S. Application Data

(62) Division of application No. 12/235,059, filed on Sep. 22, 2008.

(Continued)

(51) Int. Cl.
*A61B 17/00* (2006.01)
*A61B 90/00* (2016.01)

(52) U.S. Cl.
CPC ............... *A61B 17/0057* (2013.01); *A61B 2017/00575* (2013.01); *A61B 2017/00592* (2013.01); *A61B 2017/00601* (2013.01); *A61B 2017/00606* (2013.01); *A61B 2017/00867* (2013.01); *A61B 2017/00911* (2013.01); *A61B 2090/3933* (2016.02)

(58) Field of Classification Search
CPC .......... A61B 17/0057; A61B 17/12031; A61B 17/12109; A61B 17/12172; A61B 2017/00575; A61B 2017/00592; A61B 2017/00867; A61B 2017/00606; A61B 2017/00632; A61B 2017/12127

See application file for complete search history.

(56) References Cited

U.S. PATENT DOCUMENTS 5,192,301 A * 3/1993 Kamiya et al. ............... 606/213
5,725,552 A * 3/1998 Kotula et al. ................. 606/213
(Continued)

OTHER PUBLICATIONS

U.S. Appl. No. 11/827,590, filed Jul. 12, 2007.
U.S. Appl. No. 11/966,397, filed Dec. 28, 2007.
U.S. Appl. No. 12/040,260, filed Feb. 29, 2008.

*Primary Examiner* — Alexander Orkin
(74) *Attorney, Agent, or Firm* — Armstrong Teasdale LLP (57) ABSTRACT

Embodiments of the present invention provide medical devices and methods for occluding a target site are provided. For example, the medical device may include a tubular member having proximal and distal ends and at least one plane of occlusion. The at least one plane of occlusion may be configured to substantially occlude the patent ductus arteriosus in less than about 1 minute. In addition or alternatively, the tubular member may consist of a single layer of material and be configured to be constrained within a catheter having an outer diameter of less than about 4 French for percutaneous delivery to the patent ductus arteriosus.

20 Claims, 9 Drawing Sheets

Related U.S. Application Data (60) Provisional application No. 61/022,164, filed on Jan. 18, 2008.

(56) References Cited

U.S. PATENT DOCUMENTS

| | | | |
|---|---|---|---|
| 5,733,294 A | 3/1998 | Forber et al. | |
| 5,846,261 A | 12/1998 | Kotula et al. | |
| 5,853,422 A | 12/1998 | Huebsch et al. | |
| 5,879,366 A | 3/1999 | Shaw et al. | |
| 5,944,738 A | 8/1999 | Amplatz et al. | |
| 5,947,997 A | 9/1999 | Pavcnik et al. | |
| 6,007,544 A | 12/1999 | Kim | |
| 6,638,257 B2 | 10/2003 | Amplatz | |
| 8,034,061 B2 * | 10/2011 | Amplatz et al. | 606/151 |
| 8,313,505 B2 * | 11/2012 | Amplatz et al. | 606/200 |
| 8,398,670 B2 | 3/2013 | Amplatz et al. | |
| 8,777,974 B2 * | 7/2014 | Amplatz et al. | 606/200 |
| 9,039,724 B2 * | 5/2015 | Amplatz et al. | 606/191 |
| 9,743,918 B2 * | 8/2017 | Amplatz | A61B 17/0057 |
| 2002/0143349 A1 * | 10/2002 | Gifford et al. | 606/157 |
| 2004/0220610 A1 | 11/2004 | Kreidler et al. | |
| 2005/0228434 A1 | 10/2005 | Amplatz et al. | |
| 2005/0267527 A1 | 12/2005 | Sandoval et al. | |
| 2006/0052821 A1 | 3/2006 | Abbott et al. | |
| 2006/0241690 A1 | 10/2006 | Amplatz et al. | |
| 2006/0247680 A1 | 11/2006 | Amplatz et al. | |
| 2007/0233186 A1 | 10/2007 | Meng | |
| 2007/0265656 A1 | 11/2007 | Amplatz et al. | |
| 2007/0265658 A1 | 11/2007 | Nelson et al. | |
| 2008/0077180 A1 * | 3/2008 | Kladakis | A61B 17/0057 606/216 |
| 2008/0200945 A1 | 8/2008 | Amplatz et al. | |
| 2008/0249562 A1 | 10/2008 | Cahill | |
| 2009/0018562 A1 | 1/2009 | Amplatz et al. | |
| 2009/0062841 A1 | 3/2009 | Amplatz et al. | |
| 2009/0171386 A1 | 7/2009 | Amplatz et al. | |
| 2009/0187214 A1 | 7/2009 | Amplatz et al. | |

* cited by examiner

| Waist Diameter (A) | 3 | 3 | 4 | 4 | 4 | 5 | 5 | 6 | 6 |
|---|---|---|---|---|---|---|---|---|---|
| Nominal Length (B) | 4 | 6 | 4 | 4 | 6 | 4 | 6 | 4 | 6 |
| Disc Diameter (C) | 9 | 9 | 10 | 10 | 10 | 11 | 11 | 12 | 12 |

| CATHETER SIZE | CATHETER LENGTH (cm) | TIP ANGLE | DELIVERY CABLE LENGTH (cm) | DEVICE SIZE (mm) (WAIST DIAMETER - NOMINAL LENGTH) |
|---|---|---|---|---|
| 4 Fr | 60 | 90° | 160 | (03-04), (03-06), (04-04), (04-06) |
| 4 Fr | 80 | 90° | 195 | (03-04), (03-06), (04-04), (04-06) |
| 5 Fr | 60 | 90° | 160 | (05-04), (05-06), (06-04), (06-06) |
| 5 Fr | 80 | 90° | 195 | (05-04), (05-06), (06-04), (06-06) |

PERCUTANEOUS CATHETER DIRECTED INTRAVASCULAR OCCLUSION DEVICE

CROSS-REFERENCE TO RELATED APPLICATIONS

This application is a divisional of U.S. application Ser. No. 12/235,059, filed on Sep. 22, 2008, which is a non-provisional of application Ser. No. 61/022,164, filed on Jan. 18, 2008, all above applications of which are incorporated herein by reference in their entireties.

BACKGROUND OF THE INVENTION

I. Field of the Invention

Embodiments of the present invention generally relate to medical devices for treating certain target sites and, more particularly, relates to intravascular occlusion devices for selective occlusion of a target site anywhere in the body's circulatory system.

II. Description of the Related Art

A wide variety of intravascular devices are used in various medical procedures. Certain intravascular devices, such as catheters and guidewires, are generally used simply to deliver fluids or other medical devices to specific locations within a patient's body, such as a selective site within the vascular system. Other, frequently more complex, devices are used in treating specific conditions, such as devices used in removing vascular occlusions or for treating septal defects and the like.

In certain circumstances, it may be necessary to occlude a patient's lumen, vessel, chamber, channel, hole, or cavity such as to stop blood flow there through. One such condition known in the art is a patent ductus arteriosus (PDA), which is essentially a condition wherein two blood vessels, most commonly the aorta and pulmonary artery adjacent the heart, have a blood flow shunt between their lumens. Blood can flow directly between these two blood vessels through the passageway, compromising the normal flow of blood through the patient's vessels. Other physiologic conditions in the body occur where it is also desirous to occlude a vessel to prevent blood flow through the vessel.

Various devices have been developed for occlusion of vessels in various locations within the vasculature. Despite these techniques for facilitating occlusion, it would be advantageous to provide an improved occlusion device which offers increased flexibility, improved retention, alternate delivery methods and improved thrombogenicity within a vessel, chamber, channel, hole, cavity, or the like.

SUMMARY OF THE INVENTION

Embodiments of the present invention may be well suited for the selective occlusion of a vessel, lumen, channel, hole, cavity, or the like. One example, without limitation, of such a condition is a Patent Ductus Arteriosus (hereinafter PDA). Another example is a vessel, lumen, channel, or hole through which blood flows from one vessel to another vessel such as an Atrial Septal Defect (herein after ASD) or a Ventricular Septal Defect (herein after VSD). Other examples could be an Arterial Venous Fistula (AVF), Arterial Venous Malformation (AVM), a Patent Foramen Ovale (PFO), or a Para-Valvular Leak (PVL).

According to one embodiment, a medical device for occluding a patent ductus arteriosus is provided. The medical device includes a tubular member having proximal and distal ends and comprises at least one plane of occlusion. The at least one plane of occlusion may be configured to substantially occlude the patent ductus arteriosus in less than about 1 minute. In addition or alternatively, the tubular member may consist of at least one layer and be configured to be constrained within a catheter having an outer diameter of about 5 French and even about 4 French or smaller for percutaneous delivery.

According to various aspects of the medical device, the tubular member comprises a disk shaped portion having a first cross-sectional dimension on at least one of the proximal and distal ends and an adjacent geometrical shaped portion (e.g., a cylinder) having a second cross-sectional dimension smaller than the first cross-sectional dimension. The medical device may further include a transition segment disposed between the disk shaped portion and the geometrical shaped portion, wherein the disk and geometrical shaped portions are connected by the transition segment having a cross-sectional dimension smaller than both the disk diameter and geometrical shaped portion cross-sectional dimension. The tubular member may include a frustroconical shaped disk on each of the proximal and distal ends, wherein the geometrical shaped portion is disposed therebetween and connected to the frustroconical shaped disks with respective transition segments.

According to additional aspects of the medical device, the tubular member consists of a single layer of braided fabric comprising a plurality of braided metal strands. The metal strands may be a material selected from the group consisting of stainless steel, nickel based, cobalt based, nickel-titanium, shape memory, and super-elastic materials. The tubular member may include a plurality of planes of occlusion. For instance, a plurality of planes of occlusion may be configured to be positioned outside of the patent ductus arteriosus and a plurality of planes of occlusion are configured to be positioned within a cavity defined by the patent ductus arteriosus.

Another embodiment of the present invention is directed to a delivery system for delivering a medical device for occluding a patent ductus arteriosus. The delivery system includes a delivery device coupled to the medical device, wherein the medical device consists of a single layer of material, and a catheter configured to overlie the delivery device and constrain the medical device therein. The medical device is configured to be deployed from the catheter, wherein the delivery device and catheter are configured to be delivered bi-directionally to the patent ductus arteriosus either transarterially or transvenously and to deploy the medical device at least partially within the patent ductus arteriosus.

According to one aspect of the delivery system, the catheter has an outer diameter of about 5 French and even about 4 French or smaller. The delivery device and catheter may be configured to be delivered to the patent ductus arteriosus over a guidewire. Further, the catheter may be axially displaceable relative to the delivery device such that the medical device is configured to be deployed from the catheter in response to displacement of the catheter with respect to the delivery device.

Another embodiment of the present invention is directed to a method for occluding a patent ductus arteriosus. The method includes providing a medical device consisting of a single layer of material and constraining the medical device from a preset expanded configuration to a reduced configuration. The method also includes positioning the constrained medical device in a catheter, the catheter configured to be delivered bi-directionally, either transarterially or transvenously, and delivering the medical device to the patent ductus arteriosus either transarterially or transvenously. The method further includes deploying the medical device from the catheter at least partially within the patent ductus arteriosus such that the tubular member returns to the preset expanded configuration.

Aspects of the method include deploying the medical device such that at least one plane of occlusion is positioned outside the patent ductus arteriosus and at least one plane of occlusion is positioned within a cavity defined within the patent ductus arteriosus. The deploying step may include detaching a delivery system positioned within the catheter and coupled to the medical device, while the delivering step may include delivering the medical device over a guide wire. The method may further include imaging the patent ductus arteriosus using at least one of two-dimensional intracardiac echocardiography, angiography, magnetic resonance imaging, transesphogeal echocardiograpy, or Doppler color flow mapping. Moreover, the method may include verifying occlusion of the patent ductus arteriosus by injecting a radiopaque contrast media through the catheter and into the left atrium adjacent the deployed medical device and observing with angiography whether contrast enters the cavity defined by the patent ductus arteriosus and further whether any contrast within the cavity is stagnant.

BRIEF DESCRIPTION OF THE DRAWINGS

Having thus described the invention in general terms, reference will now be made to the accompanying drawings, which are not necessarily drawn to scale, and wherein:

DETAILED DESCRIPTION OF THE PREFERRED EMBODIMENTS

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

Embodiments of the present invention may provide an improved percutaneous catheter directed intravascular occlusion device for use in the vasculature in patients' bodies, such as blood vessels, channels, lumens, a hole through tissue, cavities, and the like, such as a patent ductus arteriosus (PDA). Other physiologic conditions in the body occur where it is also desirous to occlude a vessel or other passageway to prevent blood flow into or therethrough. These device embodiments may be used anywhere in the vasculature where the anatomical conditions are appropriate for the design.

The device may include one or more layers of occlusive material, wherein each layer may be comprised of any material that is configured to substantially preclude or occlude the flow of blood so as to facilitate thrombosis. As used herein, "substantially preclude or occlude flow" shall mean, functionally, that blood flow may occur for a short time, but that the body's clotting mechanism or protein or other body deposits on the occlusive material results in occlusion or flow stoppage after this initial time period. For instance, occlusion may be clinically represented by injecting a contrast media into the upstream lumen of the device and if little or no contrast media flows through the device wall after a predetermined period of time, then the position and occlusion of the device is adequate as would be recognized by one of ordinary skill in the art. More specifically, the time for occlusion could begin after deployment of the medical device, such as after the device has expanded and engaged the lumen and the delivery device has been disconnected, until no contrast media (as observed with fluoroscopy) flows through the device. For instance, if the medical device is implanted within a lumen and contrast media is injected on one side of the device (e.g., a high pressure side) but no contrast media is observed on the opposite side of the device (e.g. a low pressure side), then the device has substantially precluded or occluded blood flow through the device. Thus, if the medical device is implanted within a PDA and contrast media is injected into the aorta and does not flow through the device to the pulmonary artery or remains stagnant within the device, then flow through the PDA is substantially precluded or occluded. According to one embodiment of the present invention, the device is configured to occlude at least a portion of a vessel, a channel, a lumen, an opening, or a cavity in less than about 10 minutes and even less than about 5 minutes with observed occlusions in testing as low as within about 1 minute. Thus, in one embodiment, there is not "immediate occlusion," as the device does not immediately obstruct all blood flow but, rather, slows the flow of blood in order for occlusion to occur as described above. Such immediate occlusion may result in problems in fixation or positioning of the device in the lumen or may result in suction or the complete stoppage of flow which may be undesirable in some circumstances.

According to one embodiment, the device comprises at least one layer of metal fabric formed of a plurality of wire strands having a predetermined relative orientation with respect to one another. However, it is understood that according to additional embodiments of the present invention, the device may be formed using various techniques. For example, the device could be etched or laser cut from a tube such as to form an interstice geometry, or the device could comprise an occlusive material coupled to a scaffolding structure or a plurality of slices of a tubular member coupled together, such as via gluing. Moreover, it is understood that the device may comprise one or more layers of occlusive material such that the device may be a variety of occluding materials capable of at least partially inhibiting blood flow therethrough in order to facilitate the formation of thrombus.

Although the term "strand" is discussed herein, "strand" is not meant to be limiting, as it is understood the fabric may comprise one or more wires, cords, fibers, yarns, filaments, cables, threads, or the like, such that such terms may be used interchangeably.

According to one embodiment, the occluding material is at least one layer of metal fabric including a plurality of strands, such as two sets of essentially parallel generally helical strands, with the strands of one set having a "hand", i.e., a direction of rotation, opposite that of the other set. The strands may be braided, interwoven, or otherwise combined to define a generally tubular fabric.

The pitch of the strands (i.e., the angle defined between the turns of the strands and the axis of the braid) and the pick of the fabric (i.e., the number of wire strand crossovers per unit length) may be adjusted as desired for a particular application. The wire strands of the metal fabric used in one embodiment of the present method may be formed of a material that is both resilient and can be heat treated to substantially set a desired shape. Materials which may be suitable for this purpose may include a cobalt-based low thermal expansion alloy referred to in the field as Elgiloy, nickel-based high temperature high-strength "superalloys" commercially available from Haynes International under the trade name Hastelloy, nickel-based heat treatable alloys sold under the name Incoloy by International Nickel, and a number of different grades of stainless steel. A factor in choosing a suitable material for the wires strands is that the wires retain a suitable amount of the deformation induced by the molding surface (as described below) when subjected to a predetermined heat treatment and elastically return to said molded shape after substantial deformation.

One class of materials that meets these qualifications is so-called shape memory alloys. One particularly preferred shape memory alloy for use in the present method is Nitinol. NiTi alloys are also very elastic—they are said to be "superelastic" or "pseudoelastic". This elasticity may allow the device to return to a preset expanded configuration for deployment following passage in a distorted form through a delivery catheter. Moreover, other suitable materials include those that are compatible with magnetic resonance imaging (MRI), as some materials may cause heat or torque resulting from performing MRI, and some materials may distort the MRI image. Thus, metallic and/or non-metallic materials that reduce or eliminate these potential problems resulting from using MRI may be employed.

In forming a medical device according to one embodiment of the present invention, an appropriately sized piece of the fabric is cut from the larger piece of fabric which is formed, for example, by braiding wire strands to form a long tubular braid. When cutting the fabric to the desired dimensions, care should be taken to ensure that the fabric will not unravel. One can use a number of methods, including solder, braze, weld, coat, glue, clamp, tie or otherwise affix the ends of the desired length together (e.g., with a biocompatible cementitious organic material).

Furthermore, one or more layers of fabric may be employed to form a medical device. For example, two layers of metal fabric could be separately woven into tubular members, with one tubular member coaxially disposed within the second tubular member. For further discussion regarding a multi-layer braided device and techniques for fabricating such a device, see U.S. Patent Appl. Publ. No. 2007/0265656 to Amplatz et al., which is hereby incorporated in its entirety by reference.

The tubular braid used to fabricate occlusion devices according to one embodiment of the present invention may range from wire having a diameter of about 0.0015 to 0.005 in., preferably in the range of about 0.003 to 0.0045 in. The number of wires in the tubular braid may vary from about 36 to 144 but preferably is in the range of about 72 to 144. The pick count of the braid may vary from 30 to 100, and the fabric may have an average area between supporting fibers of about 0.0015 sq cm. and 0.10 sq cm.

Once an appropriately sized piece of the metal fabric is obtained, the fabric is deformed to generally conform to a surface of a molding element. Deforming the fabric will reorient the relative positions of the wire strands of the metal fabric from their initial order to a second, reoriented configuration. The shape of the molding element should be selected to deform the fabric into substantially the shape of the desired medical device when unconstrained. Once the molding element is assembled with the metal fabric generally conforming to a molding surface of that element, the fabric can be subjected to a heat treatment while it remains in contact with that molding surface. After the heat treatment, the fabric is removed from contact with the molding element and will substantially retain its shape in a deformed state.

Figure 1A:
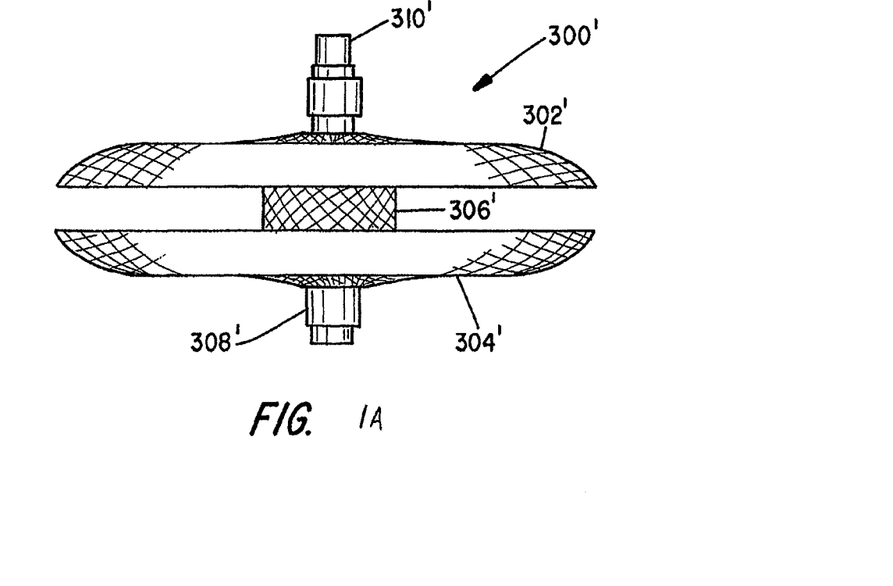
FIG. 1A depicts an occlusion device according to one embodiment of the present invention.
Figure 1B:
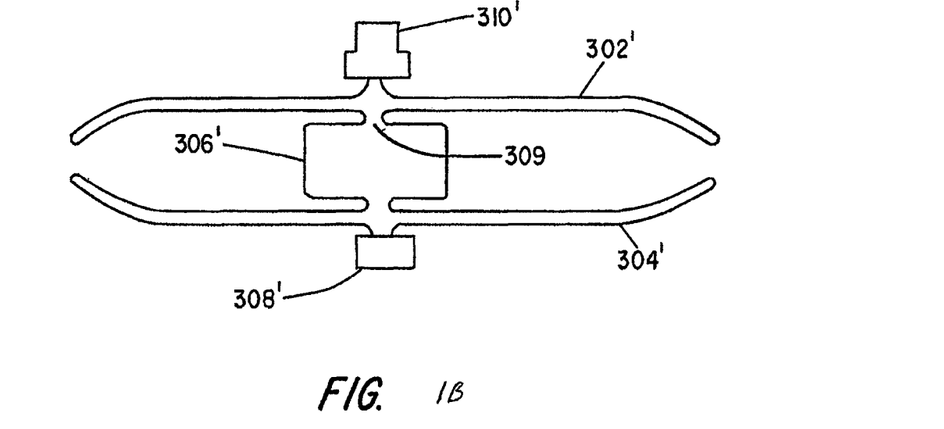
FIG. 1B is a cross-sectional view of the device of FIG. 1A.
Figure 2:
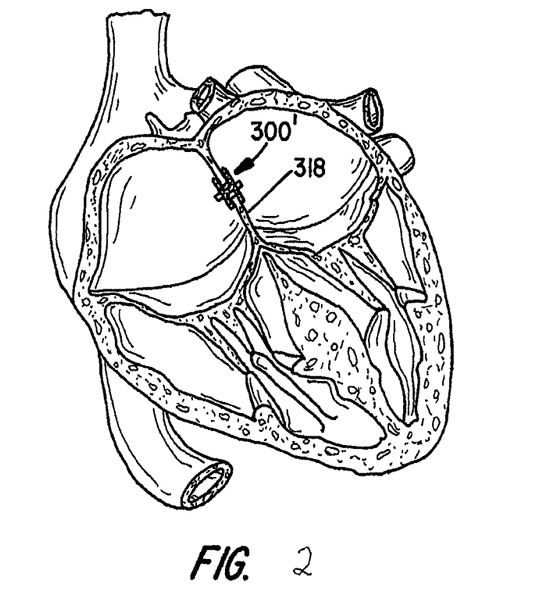
FIG. 2 is a partial sectional view of a heart, with an occlusion device positioned within the septum, according to one embodiment of the present invention.
Figure 3A:
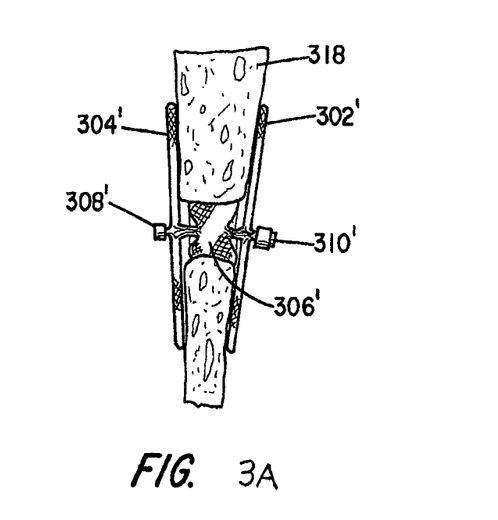
FIGS. 3A-3E are views of an occlusion device positioned within various portions of the patient's anatomy according to embodiments of the present invention.
Figure 3B:
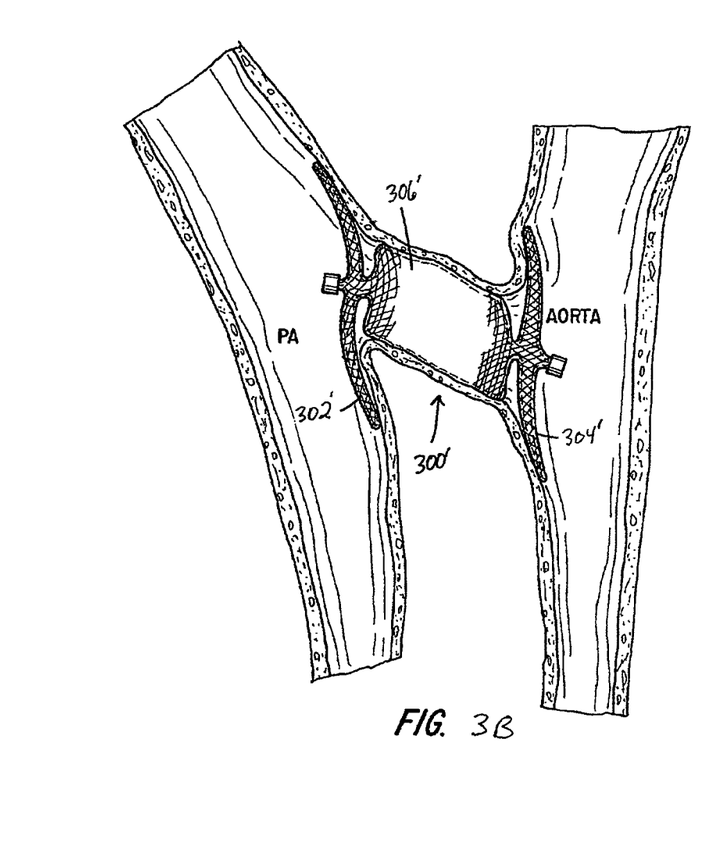
Figure 3C:
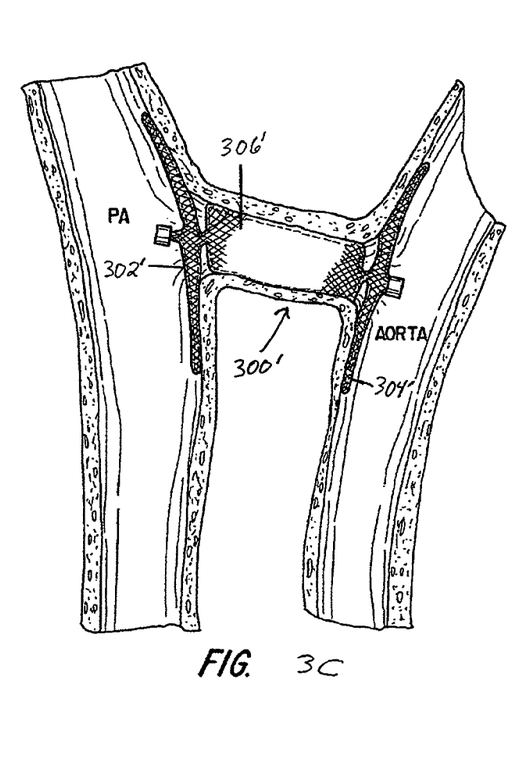
Figure 3D:
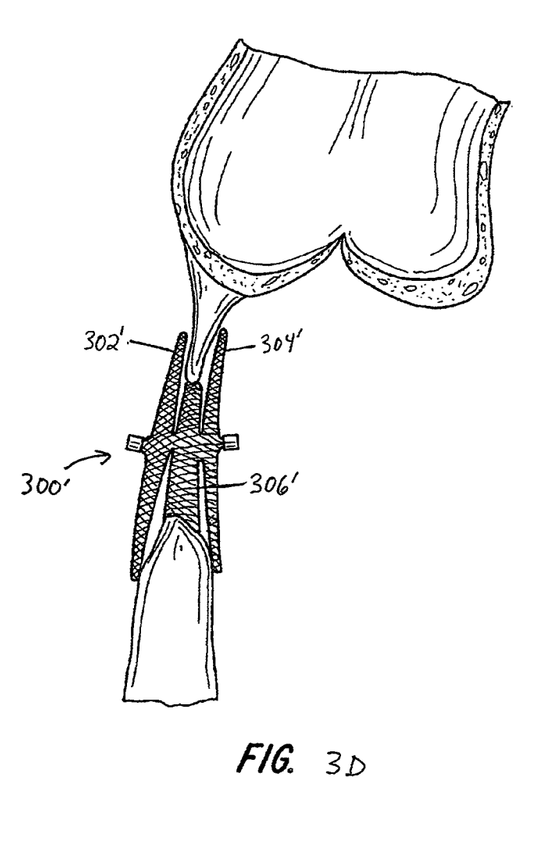
Figure 3E:
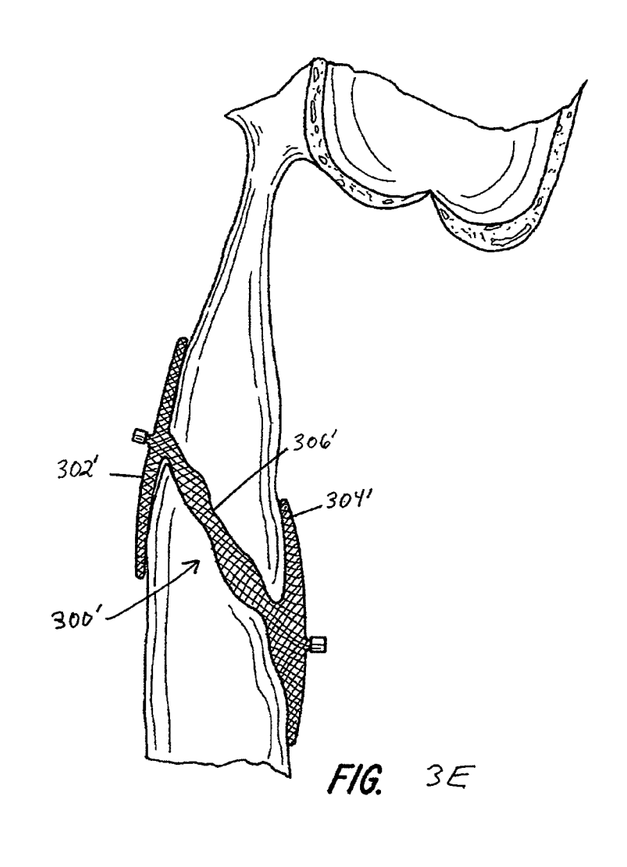
Figure 4:
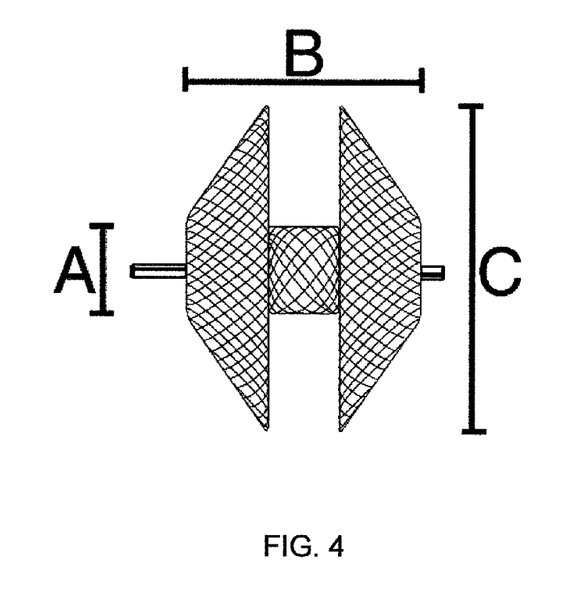
FIG. 4 is an elevational view of an occlusion device according to one embodiment of the present invention.
Figure 4A:
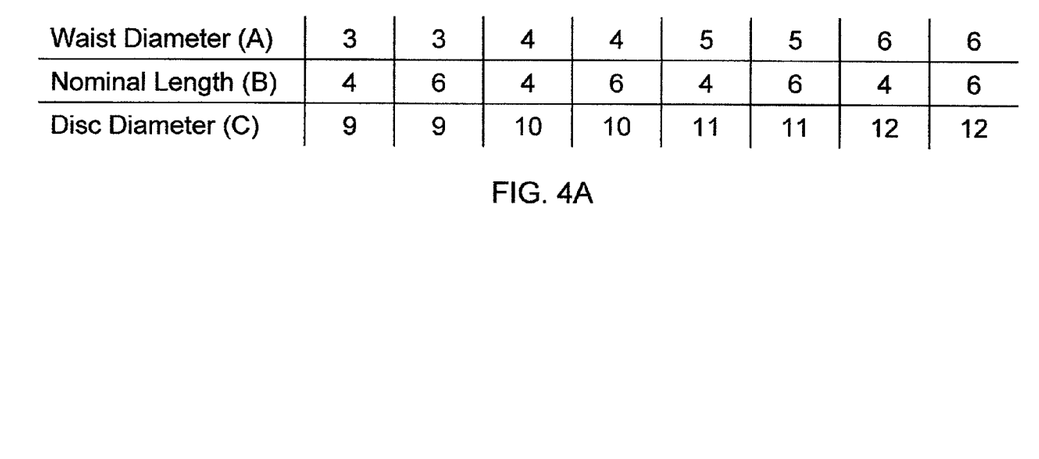
FIG. 4A illustrates exemplary dimensions for the occlusion device shown in FIG. 4 according to various embodiments of the present invention.

With reference to FIGS. 1A and 1B, the device 300' in its relaxed, unstretched state has two disks 302' and 304' aligned in spaced relation, linked together by a cylindrical segment 306'. The length of the cylindrical segment 306' may approximate the thickness of the atrial septum. The proximal 302' and distal 304' disks may have an outer diameter sufficiently larger than the cavity, opening, or the like to prevent dislodgement of the device. The disks 302' and 304' are generally frustroconical in configuration, with the larger diameter portions facing one another. Thus, as shown in FIG. 4, the disks 302' and 304' taper from a smaller diameter A to a larger diameter C. The angle extending between diameters A and C may vary and may be, for example, between about 20 and 40 degrees. Similarly, the distance between the smaller and larger diameter surfaces of each disk 302' and 304' may vary. The disks 302' and 304' are configured to extend inwardly to slightly overlap the cylindrical segment 306', which can be more clearly seen in the cross-sectional view of FIG. 1B. As also shown in FIG. 1B, the cylindrical segment 306' connects with each of the disks 302' and 304' at a diameter 309' which is smaller than both the diameter of the cylindrical segment and the disks. This configuration may allow the disks 302' and 304' to easily pivot about diameters 309' to allow the disks to align themselves with anatomical vessel walls that are not perpendicular to the aperture therebetween. FIGS. 4 and 4A illustrate the device 300' and various exemplary dimensions that may be employed according to various aspects of the present invention.

According to one embodiment, the ends of this braided fabric device 300' may be welded or clamped together with clamps 308' and 310' to avoid fraying. However, it is understood that the ends may alternately be held together by other techniques, as discussed above. The clamp 310' tying together the wire strands at the proximal end also serves to connect the device to a delivery system, which is described in further detail below. In the embodiment shown, the clamp 310' is generally cylindrical in shape and has a recess for receiving the ends of the metal fabric to substantially prevent the wires comprising the woven fabric from moving relative to one another. The clamp 310' may also have a threaded surface within the recess. The threaded recess is adapted to receive and engage the threaded distal end of a delivery device.

Those skilled in the art will appreciate that in order to speed up the occlusion of the vessel device, the device may be coated with a suitable thrombogenic agent, filled with a polyester fiber, braided with an increased number of wire strands, or include multiple layers of fabric. For example, the device may include one or more layers of thrombogenic material such as, but not limited to, polyester fiber positioned within the disks 302' and 304' and/or the cylindrical segment 306'. In particular, a layer of polyester fiber may be sized and configured to be positioned within each of the disks 302' and 304' and/or the cylindrical segment 306' and sutured circumferentially about its periphery and about the inner circumference of the body portion and disk portion, respectively. The polyester fiber is flexible and may be easily collapsed with the device for delivery through a catheter. The interwoven fiber may attach to a clot to retain the clot firmly within the device as it forms the occlusion.

Therefore, the device may include a plurality of planes of occlusion. A plane of occlusion may be any surface, whether flat or irregular in shape, that may be oriented generally transverse to the flow of blood so as to facilitate the formation of thrombus. For example, the disks 302' and 304' and the cylindrical segment 306' may include at least one plane of occlusion, such as each surface or layer of the disks and each surface or layer of the cylindrical segment. Moreover, additional layers of fabric and/or each layer of polyester fiber within the disks and/or cylindrical segment may add additional planes of occlusion. Furthermore, the one or more of planes of occlusion associated with the disks 304' and 306' may be positioned to overlie a cavity, an opening, or the like, while the one or more planes of occlusion associated with the cylindrical segment 306' may be positioned within the cavity, opening, or the like.

Figure 5:
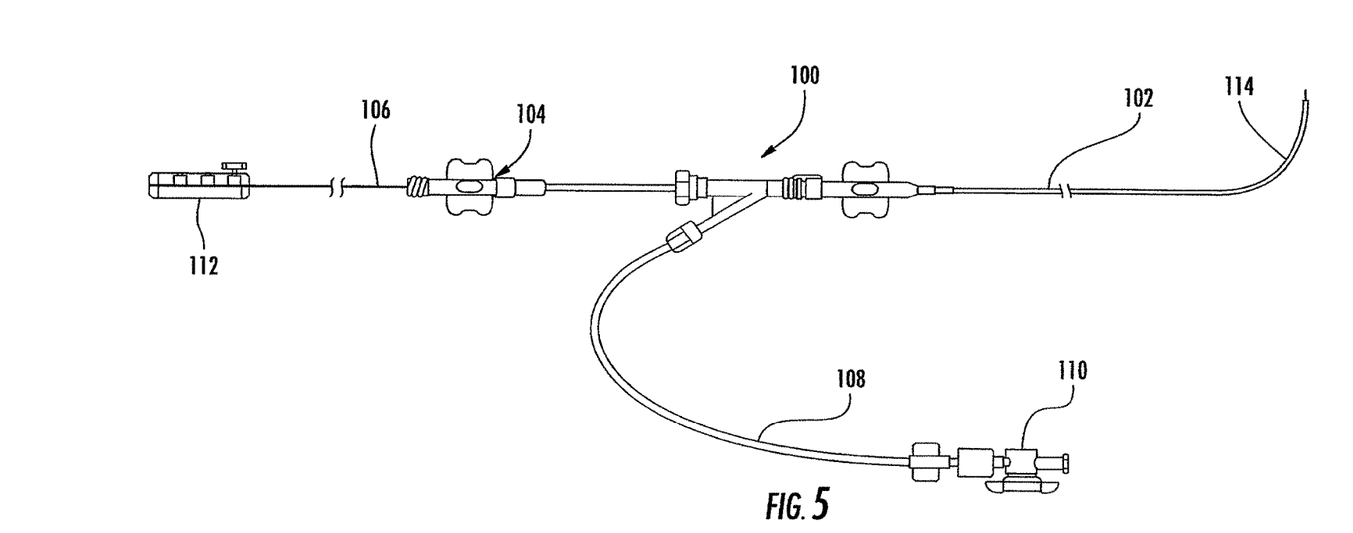
FIG. 5 is a plan view of a delivery system according to an embodiment of the present invention.
Figure 5A:
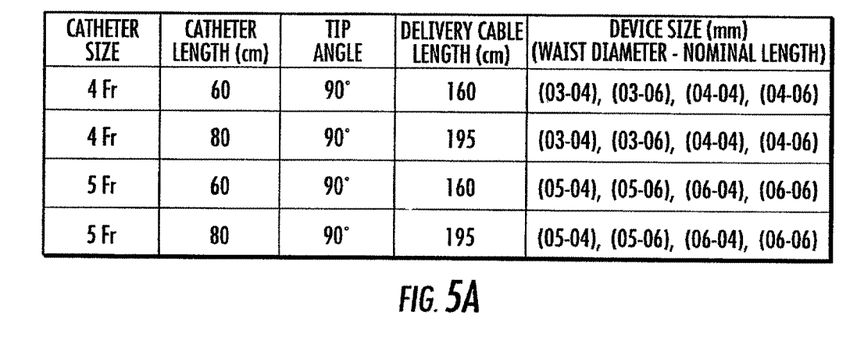
FIG. 5A illustrates exemplary dimensions for a delivery system according to various embodiments of the present invention.
Figure 6:
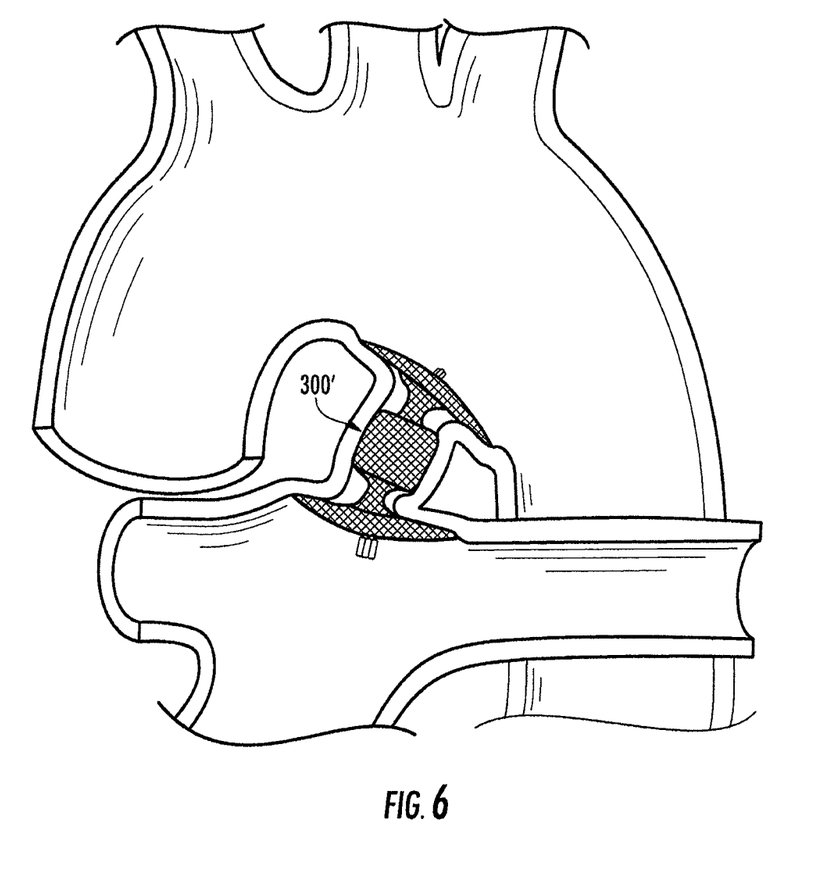
FIG. 6 is a partial sectional view of a heart, with an occlusion device positioned within the septum, according to one embodiment of the present invention.

A delivery system 100, such as that as shown in FIG. 5 may be used to deploy the device 300' in the patient's body. The delivery system 100 can take any suitable shape and may include a tube, sheath, delivery catheter 102, or the like, a metal shaft such as a guidewire 106, a loader 104, and/or vise 112, and may be used to deliver the device into the patient's lumen. The distal end 114 of the delivery system 100 may be curved, as shown in FIG. 5 in order to facilitate transarterial or transvenous delivery to the PDA. FIG. 5A also illustrates exemplary dimensions for the delivery system that may be used for various devices according to various embodiments of the present invention.

According to one embodiment, the device is loaded into the lumen by stretching the same to put it in an elongated condition. The device may be inserted into the lumen during the procedure or preassembled at a manufacturing facility, in that the devices of the present invention do not take on a permanent set when maintained in a compressed state. According to one embodiment, the device 300' may be configured to be received within a catheter having an outer diameter of less than about 5 French and even less than about 4 French. When the device is deployed out the distal end of the catheter, the device will still be retained by the delivery system. Once the proper position of the device in the vessel, body organ, or the like is confirmed, the shaft of the delivery system can be rotated about its axis to unscrew the clamp 308' or 310' from the threaded end of the delivery system. Of course the threaded connection could be at either end of the device depending on the anatomical situation and the desired or available means of access to the treatment site.

By keeping the device 300' attached to the delivery system, the operator may still retract the device back into a delivery catheter for repositioning if it is determined that the device is not properly positioned in the first attempt. In instances where the device is improperly deployed on a first try, the device may be recovered by pulling the delivery system 100 proximally, thereby retracting the device back into the delivery catheter prior to a second attempt at positioning the device relative to the vessel, body organ, or the like. The threaded attachment may also allow the operator to control the manner in which the device is deployed out of the distal end of the delivery catheter. When the device exits the delivery catheter it will tend to resiliently return to an expanded shape which was set when the fabric was heat treated. When the device springs back into this shape, it may tend to act against the distal end of the catheter, effectively urging itself forward beyond the end of the catheter. This spring action could conceivably result in improper positioning of the device. Since the threaded clamps 308' and 310' can enable the operator to maintain a hold on the device during deployment, the spring action of the device can be controlled and the operator can control the deployment to ensure proper positioning.

It is understood that the delivery system 100 may include various alternative aspects for delivering the device. For example, the delivery system may include a touhy borst and/or hemostatis valve 108 and a stop cock 110 for facilitating the delivery or withdrawal of fluids or use of instruments with the delivery device. Optionally, the device 300' could be configured with a hollow inner clamp member at one or both ends to allow a push wire or guidewire 106 to freely pass therethrough. According to one embodiment, the delivery catheter 102 sheath may have a 0.001 in thick inner layer of PTFE to lower friction for ease of device passage therethrough. For a discussion of a delivery device according to additional variations of the present invention, Applicants hereby incorporate in its entirety, U.S. patent application Ser. No. 11/827,590 to Amplatz et al., filed Jul. 12, 2007.

Figure 7:
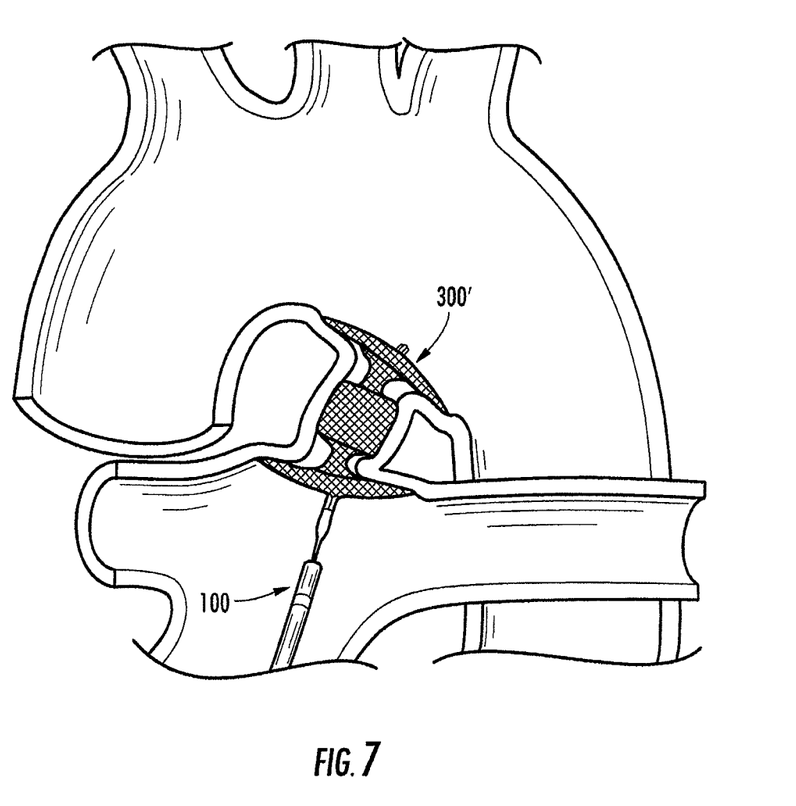
FIG. 7 is a partial sectional view of a heart, with an occlusion device being delivered transvenously, according to one embodiment of the present invention.
Figure 8:
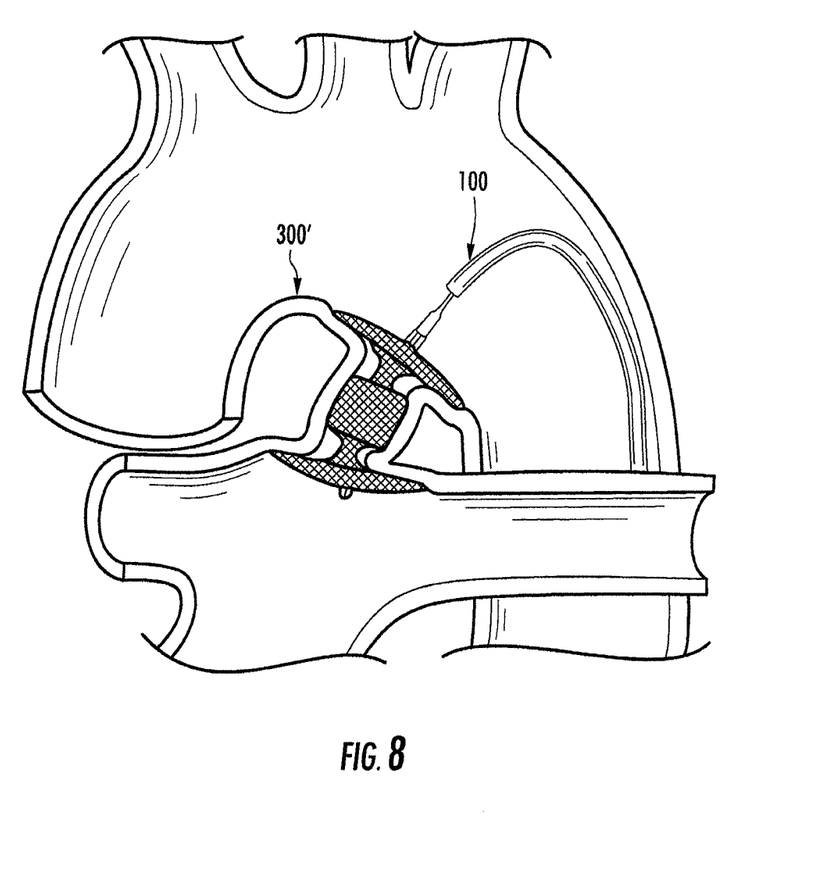
FIG. 8 is a partial sectional view of a heart, with an occlusion device being delivered transarterially, according to one embodiment of the present invention.

Generally, a method in accordance with one embodiment of the present invention includes a method of treating a physiological condition of a patient. In accordance with this method, a medical device suitable for treating the condition, which may be substantially in accordance with one of the embodiments described in detail above, is selected. The device may be delivered and properly placed using two-dimensional ICE, MRI, transesphogeal echocardigrapy, angiography, and/or Doppler color flow mapping. With the advent of two-dimensional ICE, MRI, trans-esophageal echocardiography, bi-plane angiography, and Doppler color flow mapping, the approximate anatomy of the defect can be visualized. The device that is employed will be based on the approximate size of the vessel, cavity, or the like to be occluded. Once the appropriate medical device is selected, a catheter may be positioned within a channel in patient's body to place the distal end of the catheter adjacent the desired treatment site, such as immediately adjacent or within the wall of the septum. According to one embodiment, FIGS. 7 and 8 illustrate that the device 300' may be delivered with the device 100 either via the aortic side by femoral artery access (FIG. 8) or via pulmonary artery access (FIG. 7).

The medical device can be collapsed into its collapsed configuration and inserted into the lumen of the catheter. The collapsed configuration of the device may be of any shape suitable for easy passage through the lumen of a catheter and proper deployment out the distal end of the catheter. For example, the device may have a relatively elongated collapsed configuration wherein the device is stretched along its axes for insertion into the catheter. This collapsed configuration can be achieved simply by stretching the device generally along its axis, e.g., by manually grasping opposing ends of the device and pulling them apart, which will tend to collapse the disks 302' and 304' and cylindrical segment 306' of the device 300' inwardly toward the device's axis. In this regard, the device is not unlike "Chinese handcuffs", which tend to constrict in diameter under axial tension.

The medical device may also be collapsed by drawing the delivery system coupled to the medical device proximally into an introducer tube (not shown) extending over the delivery system shaft. Drawing the delivery system proximally pulls the device into the introducer tube sized with an inside diameter to hold the medical device to a diameter to allow forward loading into a catheter.

Once the medical device is collapsed and inserted into the catheter, it may be urged along the lumen of the catheter toward the distal end of the catheter. This may be accomplished by using a delivery system or the like removably connected to the device to urge it along the catheter. When the device begins to exit the distal end of the catheter, which is positioned adjacent the desired treatment site, it will tend to resiliently return substantially entirely to its preset expanded configuration. Superelastic alloys, such as Nitinol, are particularly useful in this application because of their ability to readily return to a particular configuration after being elastically deformed to a great extent. Hence, simply urging the medical device out of the distal end of the catheter tends to properly deploy the device at the treatment site.

Although the device will tend to resiliently return to its initial expanded configuration (i.e., its shape prior to being collapsed for passage through the catheter), it should be understood that it may not always return entirely to that shape. For example, the cylindrical segment 306' is intended to have a maximum outer diameter in its expanded configuration at least as large as and preferably larger than, the inner diameter of the lumen in which it is to be deployed. If such a device is deployed in a vessel, body organ, or the like having a small lumen, the lumen will prevent the device from completely returning to its expanded configuration. Nonetheless, the device would be properly deployed because it would engage the inner wall of the lumen to seat the device therein, as detailed above.

If the device is to be used to permanently occlude a channel in the patient's body, such as the device 300', one can simply disconnect the delivery system by reversing the reversible connection to the device and retract the catheter and delivery system from the patient's body. This will leave the medical device deployed in the patient's vascular system so that it may occlude the blood vessel or other channel in the patient's body.

Embodiments shown in FIGS. 2, 3A-3E, and 6-8 illustrate how the disks 302' and 304' can assume a non-parallel relationship to intimately engage opposed walls of a septum 318 of non-uniform thickness and with the central cylindrical portion 306' expanded against the walls of the septum. The disks 302' and 304' are tapered towards the vessel, lumen, channel, hole, cavity, or the like, which allows the device to conform to a wall thickness (e.g., septum) having various lengths. Furthermore, the flexibility between the disks 302' and 304' and the cylindrical segment 306' allows the device 300' to be adaptable to a variety of abnormalities, which is illustrated by FIGS. 3A-3E and 6-8.

According to one particular embodiment of the present invention, a method for delivering a device 300' for treating a PDA is described, although it is understood that various techniques could be used according to additional aspects of the present invention. For example, the method generally involves performing a right heart catheterization and determining the diameter and length of the PDA using angiography. The appropriate sized device may be chosen based on the diameter and length determinations. A guidewire may then be introduced using an arterial or venous approach and crossed over the PDA. The delivery catheter may be delivered over the guidewire and across the PDA. The position of the delivery catheter could be confirmed using contrast medium. A delivery device or cable is passed through a loader and the device 300' screwed clockwise onto the tip of the delivery device. Once attached, the delivery device and loader may be immersed in saline solution, and the delivery device pulled into the loader. The guidewire may be slowly removed from the delivery catheter and back-bleeding allowed through the side arm valve to purge air from the delivery system. The loader may be introduced into the catheter and without rotation, the device 300' may be advanced to the distal tip of the catheter. The distal disk may be deployed and the system slowly retracted until the distal disk conforms to the vessel wall. The placement of the disk could be confirmed using fluoroscopy. While maintaining tension on the delivery device, the cylindrical segment and proximal disk may be deployed by retracting the delivery catheter. A test injection could be performed following deployment of the device in order to verify the position thereof.

While a preferred embodiment of the present invention has been described, it should be understood that various changes, adaptations and modifications may be made therein without departing from the spirit of the invention and the scope of the appended claims. For example, it is anticipated that in a double disk design that it may be desirable that only one end of the device have a small transition diameter between the disk and the adjacent middle cylindrical portion. The disks could also be other geometrical shapes if desired. It is also anticipated that the cylindrical middle or body portion may be non-concentric to one or both disks. It is further anticipated that the cylindrical portion could be various geometrical shapes, such as barrel shaped, concave, convex, tapered or a combination of shapes without departing from the invention herein. Likewise the cylindrical portion distal and proximal ends could have differing shapes, such as a recessed conical shape.

Embodiments of the present invention may provide several advantages. For example, a smaller, lower profile device that can fit through a 4 French catheter potentially allows treatment of pre-mature infants with a PDA, while current techniques typically require surgery. In addition, the device is capable of decreasing the time for occluding a vessel, lumen, channel, hole, cavity, or the like in about 1 minute or less. Moreover, the device may be capable of treating more morphologies and has increased conformability in order to decrease the incidence of device lengthening, thereby maintaining fixation of the device within the vessel, lumen, channel, hole, cavity, or the like. Furthermore, the device may be delivered bi-directionally for treating a PDA, i.e., delivery via the pulmonary artery or the aortic artery.

Many modifications and other embodiments of the invention set forth herein will come to mind to one skilled in the art to which this invention pertains having the benefit of the That which is claimed:

1. A medical device for occluding a patent ductus arteriosus, the medical device comprising:
    only one layer of braided fabric forming a tubular member having proximal and distal ends, the tubular member, in a preset expanded configuration, comprising a proximal disk-shaped portion at the proximal end and a distal disk-shaped portion at the distal end and a cylindrical segment disposed therebetween, each of the proximal and distal disk-shaped portions having a maximum cross-sectional dimension larger than the cylindrical segment, the tubular member further comprising a transition segment coupled to either of the proximal or distal disk-shaped portions and the cylindrical segment, the transition segment having a maximum cross-sectional dimension smaller than both the proximal and distal disk-shaped portions and the cylindrical segment.

2. The medical device of claim 1, further comprising a pair of transition segments, each transition segment coupled to one of the proximal or distal disk-shaped portions and the cylindrical segment, each transition segment having a maximum cross-sectional dimension smaller than both the proximal and distal disk-shaped portions and the cylindrical segment.

3. The medical device of claim 1, wherein the layer of braided fabric comprises a plurality of braided metal strands.

4. The medical device of claim 3, wherein the metal strands comprise a material selected from the group consisting of stainless steel, nickel based, cobalt based, nickel-titanium, shape memory, and super-elastic materials.

5. The medical device of claim 1, wherein the layer of braided fabric is configured to be constrained within a catheter having an outer diameter of about 5 French or smaller for percutaneous delivery.

6. The medical device of claim 1, wherein the tubular member comprises at least one plane of occlusion configured to substantially occlude the patent ductus arteriosus in less than or equal to 1 minute from the time the tubular member is deployed in the patent ductus arteriosus to a time wherein contrast media injected on one side of the tubular member in the aorta does not flow through the tubular member to the other side of the tubular member in the pulmonary artery.

7. The medical device of claim 1, wherein the proximal and distal disk-shaped portions are generally frustoconical.

8. The medical device of claim 1 further comprising a polyester fiber positioned within at least one of the proximal disk-shaped portion, the distal disk-shaped portion, and the center cylindrical portion.

9. A delivery system for delivering a medical device for occluding a patent ductus arteriosus, the delivery system comprising:
    a delivery device coupled to the medical device according to claim 1; and
    a catheter configured to overlie the delivery device and constrain the medical device therein, wherein the medical device is configured to be deployed from the catheter, and wherein the delivery device and catheter are configured to be delivered bi-directionally to the patent ductus arteriosus either transarterially or transvenously and to deploy the medical device at least partially within the patent ductus arteriosus.

10. The delivery system of claim 9, wherein the medical device comprises a plurality of planes of occlusion configured to be positioned outside of the patent ductus arteriosus and a plurality of planes of occlusion configured to be positioned within a cavity defined by the patent ductus arteriosus.

11. The delivery system of claim 9, wherein the catheter has an outer diameter of about 5 French.

12. The delivery system of claim 9, wherein the catheter has an outer diameter of about 4 French or smaller.

13. The delivery system of claim 9, wherein the delivery device and catheter are configured to be delivered to the patent ductus arteriosus over a guidewire.

14. The delivery system of claim 9, wherein the catheter is axially displaceable relative to the delivery device such that the medical device is configured to be deployed from the catheter in response to displacement of the catheter with respect to the delivery device.

15. A method for occluding a patent ductus arteriosus, the method comprising:
    providing a medical device according to claim 1;
    constraining the medical device from the preset expanded configuration to a reduced configuration;
    positioning the constrained medical device in a catheter, the catheter and device configured to be delivered bi-directionally, either transarterially or transvenously;
    delivering the medical device to the patent ductus arteriosus either transarterially or transvenously; and
    deploying the medical device from the catheter at least partially within the patent ductus arteriosus such that the medical device returns to the preset expanded configuration.

16. The method of claim 15, wherein the medical device comprises a plurality of planes of occlusion, and wherein deploying comprises deploying the medical device such that at least one plane of occlusion is positioned outside the patent ductus arteriosus and at least one plane of occlusion is positioned within a cavity defined within the patent ductus arteriosus.

17. The method of claim 15, wherein deploying comprises detaching a delivery system positioned within the catheter and coupled to the medical device.

18. The method of claim 15, wherein delivering comprises delivering the medical device over a guide wire.

19. The method of claim 15, further comprising imaging the patent ductus arteriosus using at least one of two-dimensional intracardiac echocardiography, angiography, magnetic resonance imaging, transesphogeal echocardiography, or Doppler color flow mapping.

20. The method of claim 15, further comprising verifying occlusion of the patent ductus arteriosus by injecting a radiopaque contrast media through the catheter and into the aorta downstream of the deployed medical device and observing with angiography whether contrast enters the cavity defined by the patent ductus arteriosus and further whether any contrast within the cavity is stagnant.

* * * * *